United States Patent [19]

Burkhart

[11] Patent Number: 5,222,962
[45] Date of Patent: Jun. 29, 1993

[54] ENDOSCOPIC SURGICAL INSTRUMENT FOR RELEASABLY GRASPING A CURVED NEEDLE

[76] Inventor: Stephen S. Burkhart, 201 Village Cir., San Antonio, Tex. 78232

[21] Appl. No.: 872,548

[22] Filed: Apr. 23, 1992

[51] Int. Cl.⁵ .............................................. A61B 17/00
[52] U.S. Cl. .................................. 606/148; 606/147; 606/139; 606/207
[58] Field of Search .............................. 606/205–209, 606/139, 147, 148; 81/418, 421, 302

[56] References Cited

U.S. PATENT DOCUMENTS

| | | | |
|---|---|---|---|
| 2,504,202 | 4/1950 | Kadavy | 606/147 |
| 2,642,871 | 6/1953 | Thuerig | 606/207 |
| 3,120,847 | 2/1964 | Cavaness | 606/147 |
| 3,404,677 | 10/1968 | Springer | 606/206 |
| 4,872,456 | 10/1989 | Hasson | 606/207 |
| 5,082,000 | 1/1992 | Picha et al. | 606/206 |
| 5,100,421 | 3/1992 | Christoudias | 606/147 |

FOREIGN PATENT DOCUMENTS 2210574 6/1989 United Kingdom ............... 606/206

Primary Examiner—Stephen C. Pellegrino
Assistant Examiner—Jeffrey A. Schmidt
Attorney, Agent, or Firm—Gunn, Lee & Miller

[57] ABSTRACT

An endoscopic surgical instrument for releasably grasping a curved needle, the instrument employing a handle at a first end of a shaft, the handle for operating a set of opposed jaws at a second end of the shaft. The jaws are serrated and have a channel through the top jaw and an arcuate groove in the top surface of the bottom jaw. The nose of the jaws is slotted to receive the forward portion of the curved needle while the central portion of the curved needle rests in the groove in the top surface of the bottom jaw, and the rear portion of the curved needle extends through the channel. With the jaws compressed and holding the needle in place, the surgeon may then insert the combination through a canulus to suture the tissue at a remotely-located operation site.

10 Claims, 3 Drawing Sheets

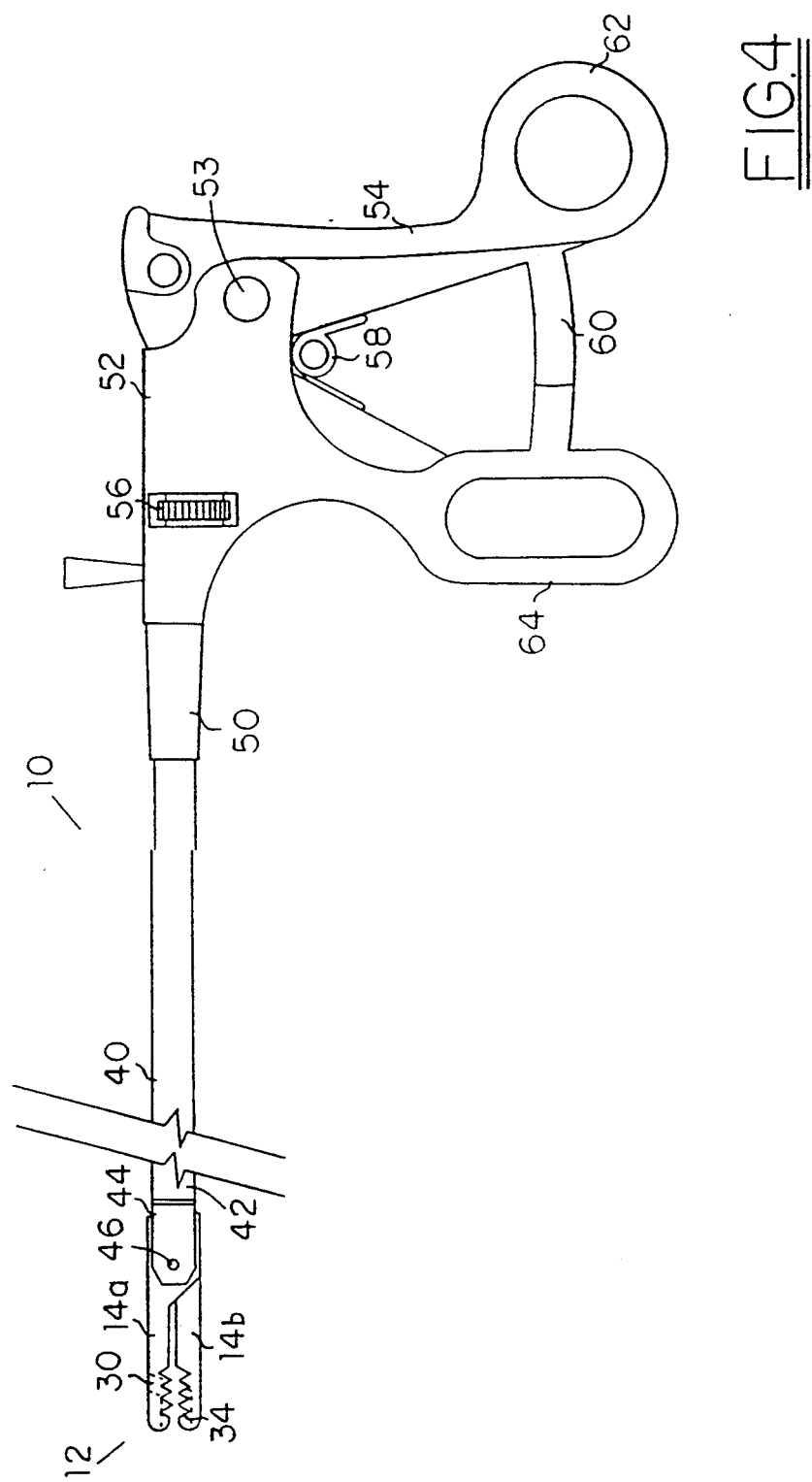

5,222,962

ENDOSCOPIC SURGICAL INSTRUMENT FOR RELEASABLY GRASPING A CURVED NEEDLE

This application incorporates by reference the specification and drawings of U.S. patent application Ser. No. 07/708,514 filed May 30, 1991.

FIELD OF THE INVENTION

Grasping instruments, more specifically, grasping instruments for use in holding a curved needle for use in arthroscopic surgery.

BACKGROUND OF THE INVENTION

Endoscopic surgery, such as arthroscopically repairing torn rotator cuffs of the shoulder requires instruments designed to operate at remote operation sites accessible through a narrow cannulae. Usually, arthroscopic suturing of tissue requires manipulation of a needle being held and controlled by a surgeon through an intermediate device, that is, in arthroscopic surgery a doctor's hands are unable to directly grasp the needle, thus a number of suturing devices have been provided to allow manipulation by the surgeon of a needle at a remote operation site.

Arthroscopic surgery, as the term is used herein, is used to describe surgery on various body parts requiring only small incisions or portals for insertion of surgical instruments manipulated externally of the body. Such surgery includes operation on the joints, and is preferable over open surgery to avoid the trauma associated with large incisions as well as the hospitalization and prolonged recovery periods required with open surgery.

Arthroscopic techniques include internal viewing for diagnosis and identification of problems as well as surgical operations such as meniscus removal or repair, shaving of irregular, roughened patella, and other surfaces and articular surface smoothing. Many surgical operations that previously required open surgery can now be performed arthroscopically. However, due to the need for direct suturing, such as a major ligament and/or cartilage repair, many operations that would benefit from arthroscopic surgery still require open surgery.

U.S. Pat. Nos. 4,602,635 and 4,621,640 to Mulhollan et al. are representative of prior art instruments for internal suturing without requiring open surgery. However, such instruments have the disadvantages of being mechanically complex and requiring multiple instrument manipulation for suturing of the tissue. The instrument of Mulhollan et al., U.S. Pat. No. 4,621,640, includes curved needle carried by a pivotal head movable to cause the needle to be set and the tissue to be sutured, the needle then being released and the instrument withdrawn to allow insertion of another instrument to pull the needle through. The Mulhollan et al. U.S. Pat. No. 4,602,635 relates to an instrument for tying knots in sutures in a manipulation area external to the body after sutures are sewn through the tissue and pushing the knots into place adjacent to the tissue.

U.S. Pat. No. 4,923,461 (Caspari et al.) discloses a method and device for suturing tissue arthroscopically including a fixed and movable jaw, the fixed jaw having a curved, hollow needle attached and the movable jaw having a slot which, when flush with the fixed jaw, allows the needle to penetrate therethrough. However, the Caspari et al. device is needlessly complex, requiring a fixed needle and limiting the ability of the surgeon to push the needle completely through a ligament.

None of the devices provide for a simple, easy-to-use instrument for grasping and manipulating a curved needle.

SUMMARY OF THE INVENTION

The present invention provides an endoscopic surgical instrument for releasably grasping a curved needle, the instrument employing a handle at a first end of a shaft, the handle for operating a set of opposed jaws articulably located at a second end of the shaft. The jaws are serrated and have a channel through the top jaw and an arcuate groove in the top surface of the bottom jaw. The nose of the jaws is slotted to receive the forward portion of the curved needle while the central portion of the curved needle rests in the groove in the top surface of the bottom jaw, and the rear portion of the curved needle extends through the channel. With the jaws compressed and holding the needle in place, the surgeon may then insert the combination through a canulus to suture the tissue at a remotely-located operation site.

BRIEF DESCRIPTION OF THE DRAWINGS

FIG. 4 is a side elevational view of applicant's present invention.

DETAILED DESCRIPTION OF THE PREFERRED EMBODIMENT

Figure 1:
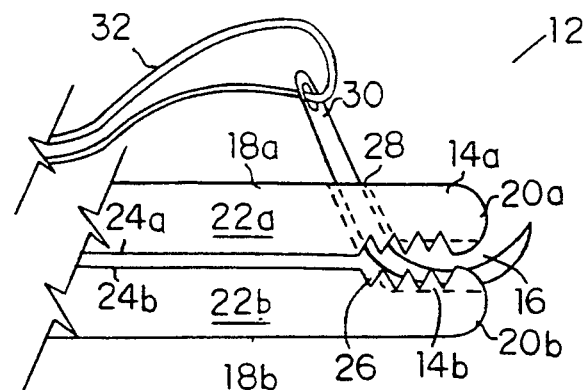
FIG. 1 is a side elevational view of the jaws of the grasping device of applicant's present invention.
Figure 2:
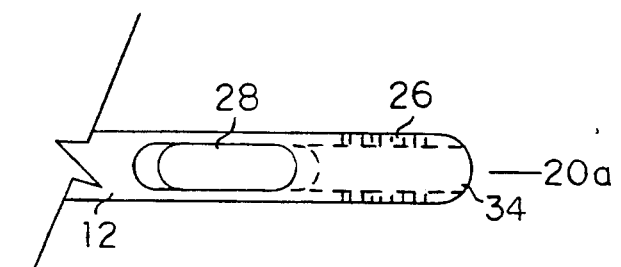
FIG. 2 is a top view of the jaws of the grasping device of applicant's present invention.
Figure 3:
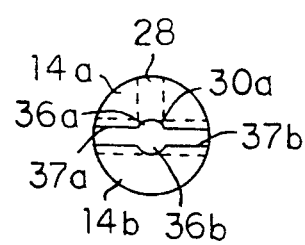
FIG. 3 is an end view of the jaws of the grasping device of applicant's present invention.

Turning now to FIGS. 1, 2, and 3 of applicant's invention, it can be seen that the jaws of applicant's invention provide for the unique ability to securely grasp a curved needle. More specifically, FIGS. 1 and 2 illustrate jaws (12) being comprised of first jaw (14a) which is articulably connected to second jaw (14b). The two jaws have top portions (18a) and (18b), front portions (20a) and (20b), side portions (22a) and (22b) (left and right side being mirror images), and inner surfaces (24a) and (24b). Matching serrated ribs may be provided by including on inner surfaces (24a) and (24b) a series of matching serrations (26).

While the jaws appear to be identical in side view, and in fact are identical overall, dimensionally speaking, they have in fact different features. Jaws (14a) and (14b) meet at mouth (16). First jaw (14a) differs from second jaw (14b) in a number of important ways. Turning now to FIGS. 1 and 2, it is seen that first jaw (14a) has a channel (28) extending from top portion (18a) through the body of first jaw (14a) and culminating at inner surface (24a). Thus, channel (28) provides sufficient room for a needle (30) to be inserted therethrough and gripped between jaws (14a) and (14b) as is illustrated in FIG. 1. Channel (28) may be dimensioned to receive comfortably therein a number of curved needles presently used in surgical operations. Channel (28) is preferably either slanted as seen in FIGS. 1 and 2 with the axis of said channel meeting the longitudinal axis of the jaws in a non-normal fashion, or may even be slightly arcuate, concave toward nose portion (20a) and (20b) of jaws (12). Such a curve in channel (28) would be provided to generally match curve of needle (30) to make for an easier fit.

A second difference between first jaw (14a) and second jaw (14b) is groove (34) located on inner surface (24b), groove (34) being wide enough to seat needle (30) and which may also be arcuate in profile to match the curved portion of needle (30). Groove (34) provides the seat for a curved portion of needle (30) which, when contained in channel (28) and gripped tightly between jaws (14a) and (14b), may be inserted through a canula (not shown) to the remotely located arthroscopic surgery site and manipulated externally by the surgeon. As can be appreciated from FIG. 2, groove (34) is coincident with the longitudinal axis of second jaw (14b), in the same plane as channel (28), and may be dish-shaped or may extend straight through nose portion (20b) as is illustrated in FIG. 3, thereby forming notch (36b) along lip (37b) of lower jaw (14b).

Turning now to FIGS. 1, 2, 3, and 4, it can be appreciated how jaws (12) provide for a unique grasping device (10) with the ability to insert and manipulate needle (30) through a small canula (not shown). More particularly, FIG. 4 illustrates jaws (12) with channel (28) in first jaw (14a) and groove (34) in second jaw (14b). Jaws (12) may be mounted pivotally on head (44) at articulation point (46). Head (44) is mounted to shaft (40) which joins at collar (50) to fixed handle (52). Fixed handle (52) is pivotally engaged at point (53) to moving handle (54). Handles (52) and (54) have grasping loops (62) and (64) attached thereto for the convenient insertion of fingers or thumb therein. FIG. 4 also illustrates spring clip (58) and ratchet (60) as two means of providing bias to handles (52) and (54) such that jaws (14a) and (14b) are urged in a closed position (as illustrated in FIGS. 1, 3, 4). Though both are pictured here together (for convenience), usually one or the other is used as means to bias jaws shut.

The device described in FIG. 4 is "old" in the art of surgical instruments with the exception of applicant's novel jaws. More specifically, devices similar, aft of the jaws, to that illustrated in FIG. 4 are available from Ethicon and as the "Endograsp ™" manufactured by Auto Suture ®. The Auto Suture ® device uses the ratchet device (60) and has an adjustable knurled knob (56) which causes shaft (40) and therefore jaws (14a) and (14b) to rotate with respect to fixed handle (52).

V. Mueller, another surgical instrument manufacturer, discloses a metal grasper with a fixed lower jaw and a spring clip, such as that illustrated at 58, for urging the jaws in a closed position. In alternative embodiments, modifications to the jaws may provide for, instead of two movable jaws, a single movable jaw and a fixed jaw.

Figure 5A:
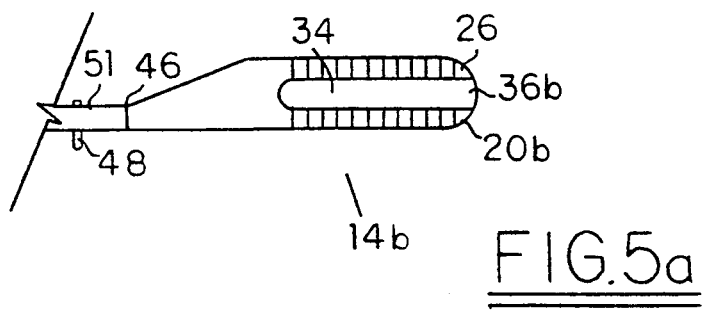
FIG. 5a is an elevational view of the lower jaw removed from the grasping instrument, illustrated in a top elevational view.
Figure 5B:
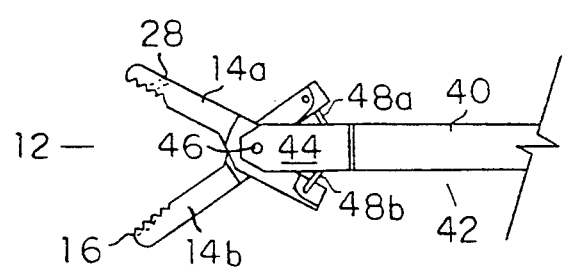
FIG. 5b is a side elevational view of the jaws of applicant's present invention in an open position.

FIGS. 5a and 5b provide additional detail to unique jaws of applicant's grasping tool (10). FIG. 5a illustrates lower jaw (14b) as removed from the grasping device and seen in top elevation. More specifically, it can be seen that groove (34) extends longitudinally across serrations (26) and terminates at nose portion (20b) at notch (36b). Extending to the distal end of front portion (20b) is blade (51) which contains articulation point (46) and activation member (48a). FIG. 5b illustrates activation members (48a) and (48b) which provide a means to transfer open and closure motion at handles (52) and (54) to jaws (14a) and (14b).

In use, needle (30), threaded with the suture, is placed with the front portion of the needle extending between the jaws as is illustrated in FIG. 1, the curved portion resting along groove (34) and the rear portion through channel (28). However, it must be pointed out at this juncture, that FIG. 1 illustrates the suture as it will be threaded for the first incision the surgeon is to make in the tissue. For the suture as it is threaded for second and subsequent stitches, the needle will be positioned as illustrated in FIG. 1 except one lead of the suture will also be threaded through channel (28). Thus, when the surgeon makes the first stitch, it will be done so by pushing the tip of the needle through the tissue (in the case of a rotator cuff, the torn tendon) and then sliding the now open jaws out through channel (28) and away from the needle and out the canula.

Thus, applicant provides a unique grasping tool similar to the Ethicon, V. Mueller, and the Schlesinger Intervertebral Disk Rongeur, but with jaws modified to provide for grasping a small, curved needle to stitch tissue at a remotely located operation site. Applicant provides jaws having at least one movable member with a channel therethrough, the second jaw having a groove therein, and a notch located in either the bottom or the top lip of the jaws, or both. The combination has proved to be both simple and effective in holding a needle in a fixed position while the instrument is manipulated externally to sew tissue.

Figure 5C:
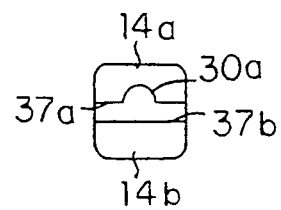
FIG. 5c is an end view of the jaws (in a closed position) illustrating an alternate preferred embodiment of applicant's present invention.

FIG. 5c illustrates an alternate preferred embodiment of jaws (12) illustrating a more rectangular cross section than the jaws illustrated in FIG. 3. Secondly, the alternate preferred embodiment illustrated in FIG. 5c has upper lip (37a) forming an upper notch (30a) to provide for seating the forward portion of curved needle (30).

Terms such as "left", "right", "up", "down", "bottom", "top", "front", "back", "in", "out" and the like are applicable to the embodiment shown and described in conjunction with the drawings. These terms are merely for the purposes of description and do not necessarily apply to the position or manner in which the invention may be constructed or used.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

I claim:

1. A grasping instrument for arthroscopic surgical use in externally manipulating a curved needle between the outside of a patient and a remote operation site, the instrument comprising:

a pair of jaws, said pair comprising a first jaw and a second jaw, the first jaw having a nose at the front end thereof and an articulation point at the rear end thereof for articulation with respect to the second jaw, the first jaw having an outer surface with a top portion, front portion, and side portions and having an inner surface, the second jaw being similar in external dimensions to the first jaw and having a nose at the front end thereof, the second jaw having an outer surface with a top portion, a front portion, and side portions and an inner surface, wherein the first jaw contains a channel therethrough from the top surface of the first jaw through to the inner surface of the first jaw;

a shaft with said pair of jaws operatively connected thereto at a first end thereof;

a pair of handles operatively connected to the second end of said shaft; and means for opening and closing said jaws;

wherein the channel of the first jaw of said pair of jaws is dimensioned to receive at least a rear portion of a curved needle therethrough, said jaws capable of securely grasping the needle so received, wherein the inner surface of the second jaw of said pair of jaws has a longitudinal groove coincident with the longitudinal axis of the second jaw and dimensioned to receive a portion of the curved needle therein when said curved needle is in the channel and is being held by the grasping device, and wherein the nose of the first jaw of said pair of jaws has a notch therein, the notch dimensioned to receive a portion of the curved needle and wherein the channel of the first jaw of said pair is arcuate and wherein the groove of the second jaw is likewise arcuate.

2. The instrument of claim 1 wherein the inner surface of each of said pair of jaws is serrated.

3. The instrument of claim 1 further including means to bias said jaws in a closed position.

4. The instrument of claim 3 wherein the inner surface of each of said pair of jaws is serrated.

5. The instrument of claim 1 further including means to rotate said jaws with respect to said pair of handles.

6. The instrument of claim 5 wherein the inner surface of each of said pair of jaws is serrated.

7. A grasping instrument for arthroscopic surgical use in externally manipulating a curved needle between the outside of a patient and a remote operation site, the instrument comprising:

a pair of jaws, said pair comprising a first jaw and a second jaw, the first jaw having a nose at the front end thereof and an articulation point the rear end thereof for articulation with respect to the second jaw, the first jaw having an outer surface with a top portion, front portion, and side portions and having an inner surface, the second jaw having an articulation point at the rear end thereof and having a nose at the front end thereof, the second jaw having an outer surface with a top portion, front portion, and side portions and an inner surface, wherein the first jaw contains a channel therethrough from the top surface of the first jaw through to the inner surface of the first jaw;

wherein the inner surface of the second jaw of said pair of jaws has an arcuate longitudinal groove coincident with the longitudinal axis of the second jaw and dimensioned to receive a portion of a curved needle therein when said curved needle is in the channel and is being held by the grasping device;

wherein the nose of the first jaw of said pair of jaws has a notch therein, the notch dimensioned to receive a portion of the curved needle;

a shaft with said pair of jaws operatively connected thereto at a first end thereof;

a pair of handles operatively connected to the second end of said shaft; and means for opening and closing said jaws, said means operatively engaging both said handles and said pair of jaws;

wherein the channel of the first jaw of said pair of jaws is arcuate and is dimensioned to receive at least the rear portion of the curved needle therethrough, said jaws capable of securely grasping the needle so received.

8. The instrument of claim 7 wherein the inner surface of each of said pair of jaws is serrated.

9. The instrument of claim 7 further including means to bias said jaws in a closed position.

10. The instrument of claim 7 further including means to rotate said jaws with respect to said pair of handles.

* * * * *